United States Patent [19]
Krumkalns

[11] 4,043,790
[45] Aug. 23, 1977

[54] METHOD OF REGULATING THE GROWTH OF AQUATIC WEEDS WITH PYRIDINE DERIVATIVES

[75] Inventor: Eriks V. Krumkalns, Indianapolis, Ind.

[73] Assignee: Eli Lilly and Company, Indianapolis, Ind.

[21] Appl. No.: 673,031

[22] Filed: Apr. 2, 1976

[51] Int. Cl.$^2$ .............................................. A01N 9/22
[52] U.S. Cl. .......................................... 71/66; 71/94; 260/290 R; 260/290 HL
[58] Field of Search .................................... 71/94, 66

[56] References Cited

U.S. PATENT DOCUMENTS

| 3,244,722 | 4/1966 | Johnston | 71/66 X |
| 3,655,359 | 4/1972 | Krumkalns et al. | 71/94 |
| 3,746,531 | 7/1973 | Doherty | 76/66 X |

Primary Examiner—Lewis Gotts
Assistant Examiner—Catherine L. Mills
Attorney, Agent, or Firm—Dwight E. Morrison; Everet F. Smith

[57] ABSTRACT

A method of regulating the growth of submerged and floating aquatic weeds which comprises adding a 2- or 4-substituted pyridinemethane or pyridinemethanol to a body of water containing the submerged and floating aquatic weeds to be regulated, in quantities sufficient to regulate the growth of the submerged and floating aquatic weeds therein. The disclosure also relates to novel compositions for carrying out the method.

10 Claims, No Drawings

METHOD OF REGULATING THE GROWTH OF AQUATIC WEEDS WITH PYRIDINE DERIVATIVES

BACKGROUND OF THE INVENTION

1. Field of the Invention

The field of the invention relates to the regulation of the growth of aquatic weeds in canals, rivers, ponds, lakes and impoundments.

2. Description of the Prior Art

The problems of controlling or regulating the growth of organisms in aqueous systems are serious and growing in severity. Submerged aquatic weeds, for example, cause major problems in water distribution and irrigation systems. The growth of such weeds in irrigation canals greatly reduces the conductivity and capacity of such systems with resulting substantial economic loss. Large sums are spent in the mechanical and other methods of removal of weed growths from irrigation canals, especially in the western parts of the United States. Because of the great difficulties involved in the mechanical removal of weeds and other undesired forms of aquatic life from irrigation canals, ponds, lakes, impoundments, etc., it has been proposed to utilize chemical control. Accordingly, various types of chemicals have been added to such bodies of water.

However, with the present emphasis on conservation, current efforts are directed toward regulating the growth, that is, limiting or inhibiting the amount of growth accomplished by the naturally occurring submerged or floating aquatic weeds without killing those weeds. This approach is being taken in order to continue to provide the natural environment for fish and other forms of marine life. A further reason is to avoid the masses of dead and rotting aquatic weeds which result when said weeds are killed by means of an aquatic herbicide, since the decomposition of the weeds decreases the amount of available oxygen present in the water. Such decaying matter, when it occurs in reservoirs and/or streams or lakes from which drinking water for cities is obtained, makes purification of the water much more difficult. Such decaying vegetation gives off an unpleasant odor when it collects in a body of water. Thus, a control of the amount of growth rather than a destruction of the submerged or floating aquatic weeds serves to overcome both pollution of the water and pollution of the air.

In the prior art, Krumkalns et al., U.S. Pat. No. 3,655,359 Apr. 11, 1972), teach the use of substituted 3-pyridylmethanes for the inhibition of the growth of the unwanted weed seeds and seedling weeds. There is no teaching in the reference that 2- and 4-substituted pyridinemethane or -methanol compounds would act to control the growth of submerged or floating aquatic weeds.

Also in the prior art, Krumkalns et al., U.S. Pat. No. 3,744,988 (July 10, 1973), teach the use of substituted 3-pyridylmethanes in a method for inhibiting sucker growth to tobacco plants. This patent is a division of U.S. Pat. No. 3,655,359, supra, and includes in its disclosure many of the same compounds disclosed in the immediately previously identified patent. There is no teaching in this reference that 2- and 4-substituted pyridinemethane or -methanol compounds would act to control the growth of submerged or floating aquatic weeds.

Van Heyningen, U.S. Pat. No. 3,396,224 (Aug. 6, 1968), teaches a method of controlling fungi pathogenic to plants by contacting the fungus-susceptible plant with a fungicidal amount of a 3-pyridylmethane derivative, mainly a 3-pyridinemethanol. I have found many of the compounds disclosed in this reference are active as aquatic growth regulators. However, there is no teaching in this reference that 2- and 4-substituted pyridinemethane or -methanol compounds would be active as aquatic growth regulators.

Van Heyningen et al., U.S. Pat. No. 3,397,273 (Aug. 13, 1968), teaches and claims a method for protecting plants from attack by phytopathogenic fungi by treating the plants with a fungicidally-effective amount of a 3-pyridylmethane. This reference makes no suggestion that 2- and 4-substituted pyridinemethane or -methanol compounds would be active as growth regulators of submerged or floating aquatic weeds.

Krumkalns, U.S. Pat. No. 3,335,148 (Aug. 8, 1967), discloses and claims the 9-(3-pyridyl) derivative of fluorene, 9-fluorneol, xanthene, 9-xanthenol, and the corresponding nonphytotoxic acid addition salts thereof alleged to be useful as antifungal and antibacterial agents. There is no teaching or suggestion in this reference that the 2- and 4-substituted pyridinemethane or -methanol compounds would be active as growth regulators of submerged or floating aquatic weeds.

Yet another reference, krumkalns, U.S. Pat. No. 3,361,753 (Jan. 2, 1968), is directed to 9-(3-pyridyl)-thioxanthene and thioxanthol derivtives, active as plant antifungal agents and as antibacterial agents. There is no teaching in this reference that the 2- and 4-substituted pyridinemtahene or -methanol compounds would be active as regulators of the growth of submerged or floating aquatic weeds.

A few 2-, 3-, and 4-substituted pyridinecarbinols are taught by Biel et al., U.S. Pat. No. 3,409,629 (Nov. 5, 1968), and are alleged to be active as hypocholesteremic agents. There is no teaching or suggestion that such compounds would be active to control the growth of submerged or floating aquatic weeds.

Another reference is German Pat. No. 1,935,292, also identified by Derwent No. 04548S, which patent teaches and claims a means for controlling plant growth, that is, restraining growth and influencing the habits of higher plants, influencing blossom and fruit formation, checking the growth of grass, and the like, using tri-arylmethylimidazoles, -pyrazoles, and -triazoles, or their salts. One of the aryl groups is taught as pyridyl. The reference does not appear to include use on aquatic weeds or plants.

Yet another reference is British Pat. No. 1,274,578, also identified by Derwent No. 23143S. This reference teaches plan growth regulators containing N-benzylimidazoles, wherein one of the substituents is a pyridyl group. These compounds are alleged to be plant growth regulators capable of inhibiting or accelerating growth, flowering and fruiting, according to the amount applied. Certain of the compounds are also alleged to be plant fungicides and bactericides.

SUMMARY OF THE INVENTION

The present invention relates to a method of regulating the growth of submerged and floating aquatic weeds by adding to the water containing such submerged and floating aquatic weeds a growth-regulating a non-herbicidal amount of 2- or 4-substituted pyridinemethane or pyridinemethanol.

DESCRIPTION OF THE PREFERRED EMBODIMENT

This invention reltes to a novel method for regulating the growth of submerged and floating aquatic weeds. More particularly, this invention relates to a novel method and compositons for regulating the growth of submerged and floating aquatic weeds which comprises adding to the water containing said weeds a growth-regulating and non-herbicidal amount of a compound selected from the group consisting of compounds of the formulae

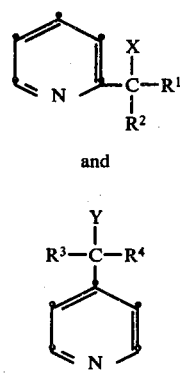

and (II)

$$R^3-\underset{\underset{\text{N}}{|}}{\overset{\overset{Y}{|}}{C}}-R^4$$

wherein
X is hydrogen or hydroxyl;
$R^1$ is hydrogen, $C_1-C_7$ alkyl, $C_3-C_6$ cycloalkyl, cyclohexylmethyl, phenyl, or monohalophenyl;
$R^2$ is $C_1-C_7$ alkyl, cyclohexyl, phenyl, $C_1-C_4$ alkoxyphenyl, monohalophenyl, cyclohexylmethyl, trifluoromethylphenyl, phenoxybutyl, or 3,4-dimethylcyclohexyl;
$R^1$ and $R^2$, when taken together with the carbon atom to which they are attached, form 9-fluoroenyl;
Y is hydrogen, hydroxyl or methoxy;
$R^3$ is hydrogen, cyclohexyl, phenyl, monohalophenyl, $C_1-C_7$ alkyl, or cyclohexylmethyl;
$R^4$ is $C_1-C_7$ alkyl, cyclohexyl, cyclohexylmethyl, monohalophenyl, phenoxybutyl, or methoxyphenyl;
$R^3$ and $R^4$, when taken together with the carbon atom to which they are attached, form 9-fluoroenyl; and the nonphytotoxic acid addition salts thereof.

In the above formulae, the $C_1-C_7$ alkyl groups are saturated straight or branched-chain alkyl and can be, illustratively, methyl, ethyl, propyl, isopropyl, n-butyl, s-butyl, t-butyl, n-amyl, isoamyl, s-amyl, n-hexyl, isohexyl, s-hexyl n-heptyl, isoheptyl, s-heptyl, and the like.

$C_3-C_6$ Cycloalkyl can be, illustratively, saturated monocyclic cycloalkyl such as cyclopropyl, cyclobutyl, cyclopentyl and cyclohexyl.

Monohalophenyl can be o-chlorophenyl, m-chlorophenyl, p-chlorophenyl, o-fluorophenyl, p-fluorophenyl, o-bromophenyl, m-bromophenyl, and the like.

$C_1-C_4$ Alkoxyphenyl can be methoxyphenyl, ethoxyphenyl, propoxyphenyl, and butoxyphenyl.

Halo or halogen is chlorine, bromine, iodine and fluorine.

The compounds useful in this invention are comveniently prepared by methods well known to the art. Thus, the 2- and 4-pyridinemethanols and derivatives thereof are prepared following the same general methods taught by Van Heyningen, U.S. 3,396,224 (August 6, 1968); and the 2- and 4-pyridylmethanes and derivatives are readily synthesized by the methods taught by Van Heyningen et al., U.S. Pat. No. 3,397,273 (Aug. 13, 1968).

Commercially unavailable intermediate ketones to be used in the syntheses of the substituted 2- and 4-pyridinemethanols are synthesized by well-known methods, as described in the following preparations.

Preparation 1

Isopropyl 4-trifluoromethylphenyl ketone

To the Grignard reagent prepared from 113 g. of 4-bromobenzotrifluoride and 13 g. of magnesium turnings in 750 ml. of anhydrous tetrahydrofuran, and heated to reflux temperature, there was added dropwise, with stirring, 35 g. of isobutyronitrile. The reaction mixture was stirred and refluxed overnight.

The reaction product mixture was cooled and the Grignard reagent decomposed by adding dilute aqueous hydrochloric acid. When addition was complete, the mixture was refluxed for about 4 hours. The mixture was cooled and the aqueous and organic layers separated. The organic layer was dried over anhydrous magnesium sulfate. The drying agent was filtered off and concentrated in vacuo to yield an oil weighing about 66 g. This product was identified by IR spectrum as isopropyl 4-trifluoromethylphenyl ketone. It was used as is without further purification.

Following the general procedure of Preparation 1 via a Grignard reaction, additional ketones were prepared and identified by NMR spectra. The compounds, together with the principal starting materials and weights thereof used in the syntheses, are listed in the preparations which follow.

Preparation 2 t-Butyl 4-fluorophenyl ketone, as an oil, weighing 20 g., from 25 g. of trimethylacetonitrile and 60 g. of 4-bromofluorobenzene.

Preparation 3 t-Butyl 4-chlorophenyl ketone, having a boiling point of about 82°-89° C./0.12 mm., and weighing 40 g., from 200 g. of trimethylacetonitrile and 461 g. of 4chlorobromobenzene.

Preparation 4

4-Chlorophenyl isopropyl ketone, having a boiling point of about 90°-110° C./1.5-2.5 mm., and weighing about 850 g., from 1915 g. of 4-chlorobromobenzene and 690 g. of isobutyronitrile.

Preparation 5

2-Chlorophenyl cyclohexyl ketone

This intermediate ketone was prepared stepwise.

Step 1. Following the general procedure of Preparation 1, and using 290 g. of 2-chlorobenzaldehyde, 50 g. of magnesium turnings, and 350 g. of bromocyclohexane, in 1500 ml. of anhydrous ethyl ether, there was obtained 410 g. of product as an oil, identified as α-(2-chlorophenyl)-α-cyclohexylmethanol.

Step 2. A mixture of 400 g. of the α-(2-chlorophenyl)-α-cyclohexylmethanol, 200 g. chromium trioxide, 800 ml. glacial acetic acid, and 250 ml. of water was heated at about 80° C. for about 2 hours.

The reaction product mixture was poured onto crushed ice, and the resulting mixture was extracted with large volumes of ethyl ether. The ether extracts were combined and dried over anhydrous magnesium sulfate. The drying agent was filtered off and the filtrate concentrated in vacuo. Crystals which appeared in the residue were filtered off, and the remaining oil distilled to yield product having a b.p. of about 102°-115° C./0.05 mm.; $N_D^{25}$ = 1.5412; weight = 127 g. Identified by NMR spectrum as 2-chlorophenyl cyclohexyl ketone.

Following the general procedure of Preparation 5, additional ketones were prepared and identified. The compounds, together with the principal starting materials and weights thereof used in the syntheses, are listed in the preparations which follow.

Preparation 6

Isopropyl 4-propoxyphenyl ketone, as an oil, weighing 34 g., from 82 g. of 4-propoxybenzaldehyde and 62 g. of isopropylbromide. Identified by TLC and IR spectrum.

Preparation 7

Cyclohexyl 4-phenoxybutyl ketone, as an oil, from 23 g. of cyclohexanecarboxaldehyde and 46 g. of phenoxybutyl bromide. Identified by IR and NMR spectra.

Preparation 8 t-Butyl 4-methoxyphenyl ketone

A mixture of 1820 g. of anisole and 758 g. of trimethylacetyl chloride was stirred in a three-neck round-bottom flask and with cooling at about 5° to 15° C., 2.2 kg. of anhydrous aluminum chloride was added over a 90 minute period. The mixture was stirred at about 15° C. for about 2 hours and then poured onto ice. The mixture was acidified and was extracted with benzene. The combined benzene extracts were washed with saturated aqueous sodium chloride solution and then dried by distilling off the benzene. A second run of the same size was made and worked up in the same way and the crude products combined and distilled at reduced pressure. There was obtained 1751 g. of product having a boiling point of about 125°-136° C./0.5-0.25 mm., identified by NMR spectrum at t-butyl 4-methyoxyphenyl ketone.

The syntheses of compounds coming within the scope of the generic formulae, supra, not previously known and useful in the novel method of this invention, are disclosed in the examples hereinbelow.

EXAMPLE 1

α-Cyclohexyl-α-phenyl-2-pyridinemethanol hydrochloride

A Grignard reagent was prepared using 33 g. of bromocyclohexane, 5 g. of magnesium turnings, and 500 ml. of ether, and to said Grignard, there was added a solution of 25 g. of 2-benzoylpyridine in 100 ml. of ether. The reaction mixture was stirred and refluxed for about 4 hours. It was then decomposed with water and the organic layer separated. The organic layer was washed with 100 ml. of water and dried. The drying agent was filtered off and the filtrate concentrated in vacuo to give a yellow oil. This oil was dissolved in about 200 ml. of commercial absolute ethanol and the solution saturated with anhydrous hydrogen chloride. An oil separated. The solvent alcohol and excess hydrogen chloride were removed in vacuo to leave a residue, which residue was recrystallized from a mixture of hot acetone and ethyl ether. There was obtained a white solid weighing 10 g., and having a melting point of about 146° C. The product was identified by NMR spectrum as α-cyclohexyl-α-phenyl-2-pyridinemethanol hydrochloride.

EXAMPLE 2

α,α-Bis(n-pentyl)-2-pyridinemethanol

To a solution of 100 ml. of a 2.3 molar n-hexane solution of butyllithium in 100 ml. of ether, cooled to a temperature of −60° to −70° C., in a nitrogen atmosphere, was added dropwise a solution of 32 g. of 2-bromopyridine in 200 ml. of ether. When the addition was complete, the reaction product mixture was stirred for about ½ hour at the same temperature.

To this solution, maintained at −65° to −70° C., in a nitrogen atmosphere, was added a solution of 27 g. of 6-undecanone in 100 ml. of ether, and when addition was complete, the mixture was stirred at a temperature of about −65 to −70° C. overnight.

The reaction product mixture was warmed to room temperature, then 100 ml. of water was added. The ether layer was separated and dried over anhydrous magnesium sulfate. The drying agent was filtered off and the filtrate was concentrated in vacuo to leave a residual oil. The oil was distilled at reduced pressure and the fraction boiling at 137°-140° C/0.5 mm. was collected. This product weighed 23 g. The product was identified by NMR spectrum and elemental analyses as α,α-bis(n-pentyl)-2-pyridinemethanol.

Analyses calculated for $C_{16}H_{27}NO$:

|   | Theoretical | Found |
|---|---|---|
| C | 77.05% | 77.23% |
| H | 10.91 | 11.04 |
| N | 5.61 | 5.71 |

Following the same procedure set forth in Example 2, additional compounds were prepared and identified. The compounds, together with the principal starting materials and weights thereof used in the syntheses, are listed in the examples set forth hereinafter.

EXAMPLE 3

α-Heptyl-α-isopropyl-2-pyridinemethanol, as an oil, and weighing 7 g., from 16 g. of 2-bromopyridine and 17 g. of 2-methyl-3-decanone. Identified by NMR spectrum and elemental analyses.

Analyses calculated for $C_{16}H_{27}NO$:

|   | Theoretical | Found |
|---|---|---|
| C | 77.05% | 77.27% |
| H | 10.91 | 10.70 |
| N | 5.61 | 5.38 |

EXAMPLE 4

α,α-Bis(n-hexyl)-2-pyridinemethanol, having a boiling point of about 146°-148° C./0.75 mm., $n_D^{25}$ 1.4846, and weighing 30 g., from 32 g. of 2-bromopyridine and 40 g. of di-n-hexyl ketone.

Analyses calculated for $C_{18}H_{31}NO$:

|   | Theoretical | Found |
|---|---|---|
| C | 77.92% | 77.74% |
| H | 11.23 | 11.00 |
| N | 5.04 | 5.24 |

EXAMPLE 5

α,α-Bis(n-pentyl)-4-pyridinemethanol, having a boiling point of about 154°–156° C./0.25 mm., and weighing 5 g., from 25 g. of 4-bromopyridine hydrochloride and 17 g. of 6-undecanone.

Analyses calculated for $C_{16}H_{27}NO$:

|   | Theoretical | Found |
|---|---|---|
| C | 77.06% | 77.01% |
| H | 10.91 | 10.94 |
| N | 5.61 | 5.52 |

EXAMPLE 6

α-Isopropyl-α-(α,α,α-trifluoro-p-tolyl)-2-pyridinemethanol, having a melting point of about 98°–100° C., and weighing 1.5 g., from 10 g. of 2-bromopyridine and 12 g. of isopropyl 4-trifluoromethylphenyl ketone.

Analyses calculated for $C_{16}H_{16}F_3NO$:

|   | Theoretical | Found |
|---|---|---|
| C | 65.08% | 65.31% |
| H | 5.46 | 5.69 |
| N | 4.74 | 4.84 |

EXAMPLE 7

α-Cyclohexyl-α-(3,4-dimethylcyclohexyl)-2-pyridinemethanol, weighing 7 g., from 16 g. of 2-bromopyridine and 22 g. of cyclohexyl 3,4-dimethylcyclohexyl ketone. Identified by NMR spectrum.

EXAMPLE 8

α-Isopropyl-α-(4-propoxyphenyl)-2-pyridinemethanol, having a melting point of about 51° C., and weighing 5 g., from 8 g. of 2-bromopyridine and 10 ml. of isopropyl 4-propoxyphenyl ketone. Identified by NMR spectrum.

EXAMPLE 9

α-(n-Hexyl)-α-(isopropyl)-2-pyridinemethanol hydrochloride, having a melting point of about 80° C., and weighing 1 g., from 10 g. of 2-bromopyridine and 9 g. of n-hexyl isopropyl ketone. Identified by NMR spectrum.

EXAMPLE 10

α-(4-Chlorophenyl)-α-isopropyl-4-pyridinemethanol, having a melting point of about 144°–145° C., and weighing 17 g., from 16 g. of 4-bromopyridine and 18 g. of p-chlorophenyl isopropyl ketone.

Analyses calculated for $C_{15}H_{16}ClNO$:

|   | Theoretical | Found |
|---|---|---|
| C | 68.83% | 68.57% |
| H | 6.16 | 6.24 |
| N | 5.35 | 5.29 |

EXAMPLE 11

α-Cyclohexyl-α-(4-phenoxy-n-butyl)-4-pyridinemethanol, having a melting point of about 77° C. and weighing 2 g., from 16 g. of 4-bromopyridine and 26 g. of 4-phenoxybutyl cyclohexyl ketone. Identified by NMR spectrum.

EXAMPLE 12

α-t-Butyl-α-(4-methoxyphenyl)-4-pyridinemethanol, having a melting point of about 137° C. and weighing 3 g., from 25 g. of 4-bromopyridine hydrochloride and 19 g. of t-butyl p-methoxyphenyl ketone.

Analyses calculated for $C_{17}H_{21}NO_2$:

|   | Theoretical | Found |
|---|---|---|
| C | 75.25% | 75.53% |
| H | 7.80 | 7.77 |
| N | 5.16 | 5.06 |

EXAMPLE 13

5-(4-Pyridyl)-10,11-dihydro-5H-dibenzo[a,d]cyclohepten-5-ol hydrochloride, having a melting point of about 214°–216° C. This is the hydrochloride salt of 5-(4-pyridyl)-10,11-dihydro-5H-dibenzo[a,d]cyclohepten-5-ol prepared from 15.8 g. of 4-bromopyridine and 20.8 g. of 5H-dibenzo[a,d]cyclohepten-5-one. The hydrochloride salt was identified by elemental analyses.

EXAMPLE 14

α-(t-Butyl)-α-(4-chlorophenyl)-2-pyridinemethanol, having a melting point of about 68°–69° C., and weighing about 4.5 g., from 16 g. of 2-bromopyridine and 19.6 g. of t-butyl 4-chlorophenyl ketone. Identified by NMR spectrum and elemental analyses.

Analyses calculated for $C_{16}H_{18}ClNO$:

|   | Theoretical | Found |
|---|---|---|
| C | 69.68% | 69.60% |
| H | 6.58 | 6.34 |
| N | 5.08 | 5.37 |

EXAMPLE 15

α-Cyclohexyl-α-isopropyl-4-pyridinemethanol, having a melting point of about 109° C., and weighing 7 g., from 16 g. of 4-bromopyridine and 15 g. of cyclohexyl isopropyl ketone. Identified by NMR spectrum.

EXAMPLE 16

α-(4-Chlorophenyl)-4-pyridinemethanol, weighing 3 g., from 25 g. of 4-bromopyridine hydrochloride and 17 g. of p-chlorobenzaldehyde. Identified by NMR spectrum.

EXAMPLE 17

α-(2-Chlorophenyl)-α-cyclohexyl-2-pyridinemethanol, having a melting point of about 95° C., weighing 12 g., from 32 g. of 2-bromopyridine and 40 g. of 2-chlorophenyl cyclohexyl ketone.

Analyses calculated for $C_{18}H_{20}ClNO$:

|   | Theoretical | Found |
|---|---|---|
| C | 71.63% | 71.35% |
| H | 6.68 | 6.70 |

-continued

|   | Theoretical | Found |
|---|---|---|
| N | 4.64 | 4.89 |

EXAMPLE 18

α-Cyclohexyl-α-(4-phenoxybutyl)-2-pyridinemethanol, as an oil, weighing about 4.5 g., from 16 g. of 2-bromopyridine and 24 g. of cyclohexyl 4-phenoxybutyl ketone. Identified by NMR spectrum.

EXAMPLE 19

α-Cyclobutyl-α-(4-fluorophenyl)-2-pyridinemethanol, having a melting point of about 63.5°–64° C., and weighing 6 g., from 12.5 g. of 2-bromopyridine and 13 g. of cyclobutyl 4-fluorophenyl ketone. Identified by NMR spectrum and elemental analyses.

Analyses calculated for $C_{16}H_{16}FNO$:

|   | Theoretical | Found |
|---|---|---|
| C | 74.69% | 74.46% |
| H | 6.27 | 6.01 |
| N | 5.44 | 5.40 |

EXAMPLE 20

α-(2-Chlorophenyl)-α-cyclohexyl-4-pyridinemethanol, having a melting point of about 167°–168° C., and weighing 12 g., from 18 g. of 4-bromopyridine and 20 g. of 2-chlorophenyl cyclohexyl ketone. Identified by NMR spectrum and elemental analyses.

Analyses calculated for $C_{18}H_{20}ClNO$:

|   | Theoretical | Found |
|---|---|---|
| C | 71.63% | 71.67% |
| H | 6.68 | 6.62 |
| N | 4.64 | 4.53 |

EXAMPLE 21

α-(t-Butyl)-α-(4-fluorophenyl)-4-pyridinemethanol, having a melting point of about 152° C., and weighing 4.5 g., from 16 g. of 4-bromopyridine and 18 g. of t-butyl 4-fluorophenyl ketone. Identified by NMR spectrum and elemental analyses.

Analyses calculated for $C_{16}H_{18}FNO$:

|   | Theoretical | Found |
|---|---|---|
| C | 74.11% | 74.25% |
| H | 7.00 | 6.87 |
| N | 5.40 | 5.39 |

EXAMPLE 22

α-Heptyl-α-isopropyl-4-pyridinemethanol, as an oil, weighing 1.2 g., from 16 g. of 4-bromopyridine and 17 g. of 2-methyl-4-decanone. Identified by NMR spectrum.

EXAMPLE 23

α-Cyclobutyl-α-(4-fluorophenyl)-4-pyridinemethanol, having a melting point of about 163° C., and weighing 3.5 g., from 11 g. of 4-bromopyridine and 12.5 g. of cyclobutyl 4-fluorophenyl ketone. Identified by NMR spectrum and elemental analyses.

Analyses calculated for $C_{16}H_{16}FNO$:

|   | Theoretical | Found |
|---|---|---|
| C | 74.69% | 74.45% |
| H | 6.27 | 6.40 |
| N | 5.44 | 5.42 |

EXAMPLE 24

α-(t-Butyl)-α-(4-methoxyphenyl)-4-pyridinemethanol, having a melting point of about 137° C., and weighing 1.7 g., from 25 g. of 4-bromopyridine hydrochloride and 19 g. of t-butyl 4-methoxyphenyl ketone. Identified by NMR spectrum and elemental analyses.

Analyses calculated for $C_{17}H_{21}NO_2$:

|   | Theoretical | Found |
|---|---|---|
| C | 75.25% | 75.53% |
| H | 7.80 | 7.77 |
| N | 5.16 | 5.06 |

EXAMPLE 25

α-(t-Butyl)-α-(4-fluorophenyl)-α-methoxy-4-pyridinemethane

This compound was prepared stepwise.

A solution was prepared of 3 g. of α-(t-butyl)-α-(4-fluorophenyl)-4-pyridinemethanol in 75 ml. of benzene and there was slowly added to the solution 10 g. of thionyl chloride. When addition was complete, the solution was refluxed for about 2 hours. The reaction product mixture was worked up by concentrating it in vacuo to remove the solvent benzene and the excess thionyl chloride. The residual oil was dissolved in methanol and sodium methylate prepared from 0.6 g. of metallic sodium and 50 ml. of absolute methanol was added. This reaction was carried out in a flask protected from atmospheric moisture. The reaction mixture was refluxed for about 2 hours. The reaction product mixture was worked up by concentrating it at reduced pressure. To the residue thus obtained, there was added methylene dichloride and water. The methylene dichloride layer was separated and the aqueous layer was again extracted with methylene dichloride. The original methylene dichloride layer was combined with the extracts, and dried over anhydrous sodium sulfate. The drying agent was filtered off and the filtrate was concentrated in vacuo. The oil that remained was chromatographed over a silica gel column, elution being accomplished with a mixture of 15 percent of acetone in toluene. There was collected 500 mg. of an oil which was identified by NMR spectrum and elemental analyses as α-(t-butyl)-α-(4-fluorophenyl)-α-methoxy-4-pyridinemethane.

Analyses calculated for $C_{17}H_{20}FNO$:

|   | Theoretical | Found |
|---|---|---|
| C | 74.70% | 74.44% |
| H | 7.38 | 7.20 |
| N | 5.12 | 5.32 |

EXAMPLE 26

α-(2-Chlorophenyl)-α-cyclohexyl-2-pyridinemethane

A mixture of 11 g. of α-(2-chlorophenyl)-α-cyclohexyl-2-pyridinemethanol, 80 ml. of aqueous 47 percent hydriodic acid, 5 ml. of concentrated aqueous hydrochloric acid, and 200 ml. of glacial acetic acid was refluxed overnight.

The reaction mixture was cooled and sodium sulfite was added. The solution was then made basic with aqueous sodium hydroxide, and extracted several times with ethyl ether. The ether extracts were combined and dried over anhydrous sodium sulfate. The drying agent was filtered off and the filtrate was concentrated in vacuo to yield an oil, weighing 6 g. The oil was identified by NMR spectrum and elemental analyses as α-(2-chlorophenyl)-α-cyclohexyl-2-pyridinemethane.

Analyses calculated for $C_{18}H_{20}ClN$:

|   | Theoretical | Found |
|---|---|---|
| C | 75.64% | 75.49% |
| H | 7.05 | 7.01 |
| N | 4.90 | 4.81 |

EXAMPLE 27

9-(2-Pyridyl)fluorene hydrochloride

This compound was prepared stepwise. In the first step, 9-(2-pyridyl)-9-fluorenol was prepared according to the procedure of Berson et al., J. Am. Chem. Soc. 87, 2887 (1965), and found to have a melting point of about 121°-125° C. The material was used as is without further purification.

A mixture of 12 g. of the fluorenol in 80 ml. of 47 percent aqueous hydriodic acid was heated under reflux for about 2 hours. The solvent was then boiled off until the reaction temperature about 140° C. After cooling, the reaction mixture was treated with excess ammonium hydroxide and the mixture was extracted with petroleum ether. The petroleum ether extracts were combined and dried over anhydrous sodium sulfate. The drying agent was filtered off and the filtrate was concentrated under reduced pressure to leave a residue. The residue was recrystallized from petroleum ether to yield product having a melting point of about 73°-75° C. and weighing about 6.6 g. It was identified by elemental analyses as 9-(2-pyridyl)fluorene.

This material was used to prepare the hydrochloride salt. The crude product was recrystallized from a mixture of methanol and ether to yield product having a melting point of about 210°-220° C. It was identified by elemental analyses as 9-(2-pyridyl)fluorene hydrochloride.

The novel method of this invention is practiced by adding the active pyridine compounds to the water containing the submerged and/or floating aquatic weeds. The compounds may be applied as dusts when admixed with a powdered solid carrier such as various mineral silicates, e.g., mica, talc, pyrophyllite, and clays. The compounds may be mixed with surface-active dispersing agents to form concentrates to facilitate dispersion in water and to improve the wetting properties when used as sprays. If desired, the compounds may be mixed with a powdered solid carrier, together with a surface-active dispersing agent, so that a wettable powder may be obtained which may be applied directly or which may be shaken up with water to make an aqueous dispersion for application in that form. The compounds may be dissolved in an oil, such as a hydrocarbon or chlorinated hydrocarbon oil, and the oil solution of the compound dispersed in water with the aid of a surface-active dispersing agent, to give a sprayable aqueous dipersion. Such surface-active dispersing agents may be anionic, nonionic, or cationic surface-active agents. Such surface-active agents are well known and reference is made to Hoffmann et al., U.S. Pat. No. 2,614,916, columns 2-4, for detailed examples of the same. The compounds useful in the present invention may also be applied by the aerosol method. Solutions for the aerosol treatment may be prepared by dissolving the compound directly in the aerosol carrier, which is liquid under pressure, but which is a gas at ordinary temperature (e.g. 20° C.) and atmospheric pressure; or, the aerosol solution may be prepared by first dissolving the compound in a less volatile solvent, and then admixing such solution with the highly volatile liquid aerosol carrier.

The invention is practiced by adding to the water containing the submerged and floating weeds a growth-regulating and non-herbicidal amount of a 21 or 4-substituted pyridine methane or -methanol compound, such that a concentration of 5-10 ppm. of the active compound is attained.

The optimum concentration of one of the compounds for any specific control problem varies with the temperature, the species to be controlled, and the shape of the water body to be treated. At higher water temperatures, less compound is generally required for a given degree of control than is needed at lower temperatures.

In considering the treatment of moving streams for the purpose of controlling flora fixed therein, special account must be taken of the fact that the compounds will pass over the area to be treated and that the concentration during the contact period is dependent upon the water flow rate, the rate of chemical addition, and the period of addition.

The novel aquatic growth regulating method and compositions for use therein are illustrated by the following experiments.

Experiment 1

The following method was used in the laboratory to evaluate the aquatic growth regulating properties of the compounds disclosed herein when used at a concentration of 10 ppm. against a representative submerged aquatic weed.

The compounds for this test were formulated in the following manner. Twenty mg. of compound was weighed into a 12 ml. disposable vial. To the vial containing the compound were added 1 ml. of acetone and 9 ml. of aqueous 0.1 percent polyoxyethylene sorbitan monooleate. To obtain the test concentration of 10 ppm., 4.00 ml. of this stock solution was added to 785 ml. of water in a plastic water in a plastic container. The plastic containers used were flowerpot-shaped, having a bottom diameter of 9 cm., a top diameter of 11.5 cm. and a height of 13.5 cm.

Terminal pieces of Florida elodea, *Hydrilla verticillata* (L.F.), (hereinafter identified as hydrilla), 10 cm. long, without branching, were prepared for testing. Three such cuttings were placed in each plastic container holding 785 ml. of water to which water the formulated test compound had been added, along with 3 ml. of Hoagland's Nutrient solution. Three 10 cm. cuttings of hydrilla were placed in each of several control containers of water, with the amount of solvent used to formulate the test compound also in such container.

After a period of two to three weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC), and the quotient multiplied by 100 to give a percent inhibition. The calculations were carried out using the following formula:

$$\frac{\text{Total combined length of Replicates}}{\text{Number of Replicates}} = \text{Average Length}$$

Avg. Length − 10 cm. = Avg. Increased Growth $$\left(1 - \frac{\text{Avg. Increased Growth}}{\text{Avg. Increased Growth SC}}\right) \times 100 = \% \text{ Inhibition}$$

The compounds employed in this experiment, as well as in one or more of the experiments described hereinafter, are identified as follows:

1. α-(2-Chlorophenyl)-α-cyclohexyl-2-pyridylmethane
2. α-Cyclohexyl-α-(3,4-dimethylcyclohexyl)-2-pyridinemethanol
3. α-Cyclohexyl-α-phenyl-2-pyridinemethanol·HCl
4. α-Isopropyl-α-(4-propoxyphenyl)-2-pyridinemethanol
5. α,α-Bis(n-pentyl)-2-pyridinemethanol
6. α,α-Bis(n-hexyl)-2-pyridinemethanol
7. 2-(4-Chlorobenzyl)pyridine
8. 9-(2-Pyridyl)fluorene·HCl
9. α-Hexyl-α-isopropyl-2-pyridinemethanol
10. α-Isopropyl-α-(α,α,α-trifluoro-p-tolyl)-2-pyridinemethanol
11. α-Cyclohexyl-α-(4-phenoxybutyl)-2-pyridinemethanol
12. α-(t-Butyl)-α-(4-chlorophenyl)-2-pyridinemethanol
13. α-Heptyl-α-isopropyl-2-pyridinemethanol
14. α-Cyclobutyl-α-(4-fluorophenyl)-2-pyridinemethanol
15. 4-Pyridyl diphentylmethane
16. α-(2-Chlorophenyl)-α-cyclohexyl-4-pyridinemethanol
17. 4-(4-Chlorobenzyl)pyridine
18. 4-(t-Butyl)pyridine
19. α,α-Bis(n-pentyl)-4-pyridinemethanol
20. α-(4-Chlorophenyl)-α-isopropyl-4-pyridinemethanol
22. α-(t-Butyl)-α-(4-methoxyphenyl)-4-pyridinemethanol
23. α-(4-Chlorobenzyl)-4-pyridinemethanol
24. α-Cyclohexyl-α-(4-phenoxybutyl)-4-pyridinemethanol
25. α-Cyclohexyl-α-isopropyl-4-pyridinemethanol
26. α-(t-Butyl)-α-(4-fluorophenyl)-4-pyridinemethanol
27. α-Heptyl-α-isopropyl-4-pyridinemethanol
28. α-Cyclobutyl-α-(4-fluorophenyl)-4-pyridinemethanol
29. α-(t-Butyl)-α-(4-fluorophenyl)-α-methoxy-4-pyridinemethanol The results of the tests, run at a concentration of 10 ppm. of compound, are set forth in the table which follows. In the table, column 1 identifies the test compound; column 2 lists the percent growth inhibition of hydrilla observed.

Table 1
Substituted 2- and 4-Pyridine Derivatives

| Compound | Approx. % Growth Inhibition |
|---|---|
| 1 | 58 |
| 2 | 75 |
| 3 | 62 |
| 4 | 50 |
| 5 | 100 |
| 6 | 78 |
| 7 | 52 |
| 8 | 72 |
| 9 | 79 |
| 10 | 66 |
| 11 | 78 |
| 12 | 98 |
| 13 | 91 |
| 14 | 53 |
| 15 | 57 |
| 16 | 51 |
| 17 | 94 |
| 18 | 86 |
| 19 | 98 |
| 20 | 93 |
| 21 | 74 |
| 22 | 79 |
| 23 | 88 |
| 24 | 57 |
| 25 | 58 |
| 26 | 100 |
| 27 | 60 |
| 28 | 95 |

The results obtained in the experiment described are reported above show that the substituted pyridine compounds disclosed herein are effective at 10 ppm. concentration in the claimed method of regulating the growth of submerged and floating aquatic weeds.

I claim:
1. A method for inhibiting the growth of submerged and floating aquatic weeds which comprises adding to the water containing said weeds an amount sufficient to provide a growth-inhibiting and non-herbicidal concentration of a compound selected from the group consisting of compounds of the formulae:

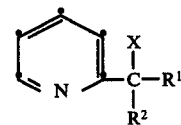
(I)

and

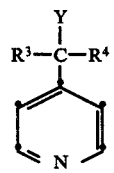
(II)

wherein
X is hydrogen or hydroxyl;
R¹ is hydrogen, $C_1$–$C_7$ alkyl, $C_3$–$C_6$ cycloalkyl, cyclohexylmethyl, phenyl, or monohalophenyl;
R² is $C_1$–$C_7$ alkyl, cyclohexyl, phenyl, $C_1$–$C_4$ alkoxyphenyl, monohalophenyl, cyclohexylmethyl, trifluoromethylphenyl, phenoxybutyl, or 3,4-dimethylcyclohexyl;
R¹ and R², when taken together with the carbon atom to which they are attached, form 9-fluorenyl;
Y is hydrogen, hydroxyl or methoxy;
R³ is hydrogen, cyclohexyl, phenyl, monohalophenyl, $C_1$–$C_7$ alkyl, or cyclohexylmethyl;

R[4] is $C_1$-$C_7$ alkyl, cyclohexyl, cyclohexylmethyl, monohalophenyl, phenoxybutyl, or methoxyphenyl;

R[3] and R[4], when taken together with the carbon atom to which they are attached, form 9-fluorenyl; and the nonphytotoxic acid addition salts thereof.

2. The method of claim 1 wherein the growth-inhibiting and non-herbicidal concentration of the active compound ranges from about 5 to about 10 ppm.

3. The method of claim 1 wherein the active compound is selected from the group consisting of compounds of the formulae

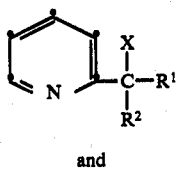
(I)

and

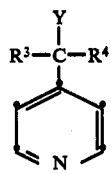
(II)

wherein
X is hydroxyl;
R[1] is $C_3$-$C_5$ alkyl;
R[2] is $C_5$-$C_7$ alkyl or 4-chlorophenyl;
Y is hydroxyl;
R[3] is $C_3$-$C_5$ alkyl or cyclohexyl;
R[4] is $C_5$-$C_7$ alkyl, 4-chlorophenyl or 4-phenoxybutyl; and
the nonphytotoxic acid addition salts thereof.

4. The method of claim 1 wherein the active compound is α-(t-butyl)-α-(4-chlorophenyl)-2-pyridinemethanol.

5. The method of claim 1 wherein the active compound is α-heptyl-α-isopropyl-2-pyridinemethanol.

6. The method of claim 1 wherein the active compound is α,α-bis(n-pentyl)-2-pyridinemethanol.

7. The method of claim 1 wherein the active compound is α,α-bis(n-pentyl)-4-pyridinemethanol.

8. The method of claim 1 wherein the active compound is α-(4-chlorophenyl)-α-isopropyl-4-pyridinemethanol.

9. The method of claim 1 wherein the active compound is α-cyclohexyl-α-(4-phenoxybutyl)-4-pyridinemethanol.

10. The method of claim 1 wherein the active compound is α-heptyl-α-isopropyl-4-pyridinemethanol.

* * * * *

UNITED STATES PATENT OFFICE
CERTIFICATE OF CORRECTION

Patent No. 4,043,790          Dated  August 23, 1977

Inventor(s)  Eriks V. Krumkalns

It is certified that error appears in the above-identified patent and that said Letters Patent are hereby corrected as shown below:

Column 1, line 51: "3,655,359 Apr." should read --3,655,359 (Apr.--

Column 2, line 21: "9-fluorneol" should read --9-fluorenol--.

Column 2, line 28: "krumkalns" should read --Krumkalns--.

Column 2, line 30: "derivtives" should read --derivatives--.

Column 2, line 33: "pyridinemtahene" should read --pyridinemethane--.

Column 2, line 54: "plan" should read --plant--.

Column 3, line 4: "reltes" should read --relates--.

Column 3, line 46: "9-fluoroenyl" should read --9-fluorenyl--.

Column 3, line 64: "comven-" should read --conven---.

Column 4, line 46: "4chloro-" should read --4-chloro---.

Column 5, line 9: "$N_D^{25}$" should read --$n_D^{25}$--.

Column 11, line 32: "temperature about" should read --temperature reached about--.

Column 11, line 68: "dipersion" should read --dispersion--.

UNITED STATES PATENT OFFICE
CERTIFICATE OF CORRECTION

Patent No. 4,043,790　　　　　　　Dated August 23, 1977

Inventor(s) Eriks V. Krumkalns

It is certified that error appears in the above-identified patent and that said Letters Patent are hereby corrected as shown below:

Column 12, line 17:　"21" should read --2---.

Column 12, line 52:　"ml. of water in a plastic water in a" should read --ml. of water in a--.

Column 13, line 42:　"diphentylmethane" should read --diphenylmethane--.

Signed and Sealed this

*Twenty-first* Day of *February 1978*

[SEAL]

Attest:

RUTH C. MASON　　　　　　　LUTRELLE F. PARKER
*Attesting Officer*　　　*Acting Commissioner of Patents and Trademarks*